(12) United States Patent
Schaeffer-Korbylo et al.

(10) Patent No.: US 11,471,394 B2
(45) Date of Patent: Oct. 18, 2022

(54) ORAL CARE COMPOSITIONS CONTAINING DEOXY SUGAR ANTIMETABOLITES

(71) Applicants: Colgate-Palmolive Company, New York, NY (US); The Forsyth Institute, Cambridge, MA (US)

(72) Inventors: Lyndsay Schaeffer-Korbylo, Flemington, NJ (US); Jorge Frias-Lopez, Boston, MA (US)

(73) Assignees: COLGATE-PALMOLIVE COMPANY, New York, NY (US); THE FORSYTH INSTITUTE, Cambridge, MA (US)

( * ) Notice: Subject to any disclaimer, the term of this patent is extended or adjusted under 35 U.S.C. 154(b) by 0 days.

(21) Appl. No.: 16/884,958

(22) Filed: May 27, 2020

(65) Prior Publication Data

US 2020/0289393 A1 Sep. 17, 2020

Related U.S. Application Data

(62) Division of application No. 14/777,461, filed as application No. PCT/US2014/026013 on Mar. 13, 2014, now abandoned.

(60) Provisional application No. 61/792,953, filed on Mar. 15, 2013.

(51) Int. Cl.
| | |
|---|---|
| *A61K 8/60* | (2006.01) |
| *A61Q 11/00* | (2006.01) |
| *A61K 8/69* | (2006.01) |
| *C07H 5/06* | (2006.01) |
| *C07H 5/02* | (2006.01) |
| *C07H 3/08* | (2006.01) |

(52) U.S. Cl.
CPC .................. *A61K 8/60* (2013.01); *A61K 8/69* (2013.01); *A61Q 11/00* (2013.01); *C07H 3/08* (2013.01); *C07H 5/02* (2013.01); *C07H 5/06* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 3,940,476 A | 2/1976 | Haas | |
| 4,143,126 A * | 3/1979 | Gaffar | A61K 8/25 424/49 |
| 2007/0042339 A1 * | 2/2007 | Toner | A01N 1/0221 435/2 |
| 2007/0166242 A1 | 7/2007 | Kross et al. | |
| 2009/0053378 A1 * | 2/2009 | Prakash | A23L 27/88 426/548 |
| 2011/0003758 A1 | 1/2011 | Priebe et al. | |
| 2015/0297490 A1 * | 10/2015 | Kim | A61K 31/047 424/55 |

FOREIGN PATENT DOCUMENTS

| | | | |
|---|---|---|---|
| EP | 0055109 | 6/1982 | |
| EP | 0055109 A2 * | 6/1982 | ............ A61Q 11/00 |
| EP | 2098227 | 9/2009 | |
| EP | 2124966 | 12/2009 | |
| JP | 2006/347941 | 12/2006 | |
| KR | 2013/0063887 | 6/2013 | |
| WO | WO 2008/093303 | 8/2008 | |
| WO | WO 2009/108926 | 9/2009 | |
| WO | WO 2011/019342 | 2/2011 | |

OTHER PUBLICATIONS

Dashper (Dashper, S.G., & Reynolds, E.C., Characterization of Transmembrane Movement of Glucose and Glucose Analogs in *Streptococcus mutans* Ingbritt, J. Bacteriol. (1990) pp. 556-563). (Year: 1990).*
Acta Microbiologica Sinica, 45:930-935 (2005) (No translation available).
Dashper, S.G., et al., "Characterization of Transmembrane Movement of Glucose and Glucose Analogs in *Streptococcus mutans* Ingbritt," J. Bacteriol, 172(2):556-563 (1990).
Fitzgerald et al., "Inhibition of Caries in hamsters by 2-Deoxy-D-glucose," J. Dent. Res., 56: 1431, (1977).
International Search Report of International Application No. PCT/US2014/026013 dated Jun. 4, 2014, 4 pages.
Keevil, C.W., et al., Protonmotive force driven 6-deoxyglucose uptake by the oral pathogen, *Streptococcus mutans* Ingbritt, Arch. Microbiol., 146:118-124 (1986).
Oral Microbiology, Sichuan University, Chapter 7 Section 6 Item 1 (2002) (No translation available).

* cited by examiner

*Primary Examiner* — Dominic Lazaro
(74) *Attorney, Agent, or Firm* — Hoxie & Associates LLC

(57) ABSTRACT

Described herein are oral care compositions comprising a deoxy sugar antimetabolite and methods of inhibiting microbial biofilm formation and/or degrading a microbial biofilm in a subject.

10 Claims, No Drawings

ORAL CARE COMPOSITIONS CONTAINING DEOXY SUGAR ANTIMETABOLITES

CROSS-REFERENCE TO RELATED APPLICATIONS

This application is a divisional of U.S. patent application Ser. No. 14/777,461 filed Sep. 15, 2015, which is a National Stage Entry under 35 U.S.C. § 371 of PCT Application No. PCT/US2014/026013, filed on Mar. 13, 2014, which claims benefit of and priority to U.S. Provisional Patent Application No. 61/792,953, filed on Mar. 15, 2013, the contents of each of which are incorporated herein by reference in their entireties.

BACKGROUND

An antimetabolite is a substance that closely resembles an essential cell metabolite. An antimetabolite competes with, interferes with, or replaces the essential metabolite in physiological reactions, thereby disrupting the cell's normal metabolic functioning. It is known to use antimetabolites for therapeutic purposes. For example, sulfanilamides are antimetabolites that as act as analogues of para-aminobenzoic acid. These compounds disrupt bacterial, but not human, metabolism and are therefore used to eradicate bacterial infections in humans. Methotrexate and 5-fluorouracil are further examples of antimetabolites which are used to treat a variety of cancers.

Glucose antimetabolites are known in the art. For example, 2-deoxy-D-glucose is a glucose molecule which is taken up by glucose transporters of the cell. However, 2-deoxy-D-glucose has the 2-hydroxyl group replaced by hydrogen so that, unlike glucose, it cannot undergo further glycolysis.

Therapeutic uses of glucose antimetabolites have been described in the art. For example, US2011 0003758A1 and WO2009108926A1 describe the use of 2-deoxy-2-fluoro hexopyranose derivatives and related glycolysis inhibitors for the treatment of brain tumors. EP2124966A2 describes the incorporation of glucose antimetabolites into food compositions for lowering blood levels of C-reactive protein, and consequently for decreasing inflammation and stress.

More specifically, glucose antimetabolites have also been known to be used in the oral care context with regard to the inhibition of caries. Examples include the inhibition of caries in hamsters by 2-deoxy-D-glucose (Fitzgerald et al., J. Dent. Res., 1977; 56: 1431) and the use of 2-deoxy-D-glucose and glucosamine in compositions to inhibit the carbohydrate induced production of acid by human dental plaque bacteria (EP 0055109).

However, a problem in the art is that use of antibacterial agents to reduce bacteria in the oral cavity can also result in the reduction of wanted bacteria and disrupting the attainment of a healthy microflora. Moreover, showings of antibacterial effect are not necessarily correlative for the reduction or inhibition of biofilm formation which is especially useful for those patients suffering from gingivitis or periodontitis.

Biofilm is a structured group of microorganisms encapsulated within a self-developed polymeric extracellular matrix. Biofilms are typically adhered to a living or inert surface. In the human or animal body, biofilms can form on any internal or external surface. Biofilms have been found to be involved in a wide variety of microbial infections in the body and cause a number of conditions including urinary tract infections, middle-ear infections, and in particular, diseases of the oral cavity.

A plaque biofilm is a soft deposit that forms on dental surfaces, and provides a locus for calculus or tartar formation. As such, plaque biofilm is implicated in the occurrence of gingivitis, periodontitis, caries and other forms of periodontal disease. Plaque biofilm adheres firmly to dental surfaces and is removed only with difficulty even through a rigorous brushing regimen. Moreover, plaque biofilm rapidly reforms on the tooth surface after it is removed.

Microorganisms present in a biofilm have significantly different properties from free-floating microorganisms of the same species. This is because within a biofilm, the polymeric extracellular matrix acts to protect the microorganisms from the surrounding environment, and allows the microorganisms to cooperate and interact in various ways which are not exhibited by free-floating microorganisms. These complex communities of microorganisms present a unique challenge in that they are often resistant to classical means of antimicrobial control.

It is known in the art to incorporate antimicrobial agents in oral compositions which destroy or retard the growth of bacteria. However, bacteria living in a biofilm exhibit increased resistance to known antimicrobial agents because the dense extracellular matrix and the outer layer of cells protect the interior of the biofilm from the effects of the antimicrobial agents. Therefore, known antimicrobial agents often do not have the same effect on bacteria present in a biofilm.

Additionally, many antimicrobial agents are incompatible or unstable with other oral care active ingredients, are difficult to deliver in vivo, or may inactivate other desirable additional oral care ingredients.

Therefore, there is a need to provide improved agents for use in oral care compositions which effectively reduce/inhibit biofilm formation and/or degrade biofilms via non-antibacterial means of biofilm control (thereby eliminating the risk of resistance), are compatible with other oral care active ingredients, are readily delivered in vivo, and/or which do not inactivate other desirable oral care ingredients or disrupt the healthy microflora of the oral cavity and/or do not require the use of an additional antibacterial agent.

BRIEF SUMMARY

The present invention relates to oral care compositions containing deoxy sugar antimetabolites and methods of inhibiting microbial biofilm formation and/or degrading a microbial biofilms.

In a first aspect, the present invention provides an oral care composition comprising a glucose antimetabolite in an amount of less than about 0.7 wt. % based on the total weight of the composition.

Optionally, the glucose antimetabolite is present in the composition at a concentration of from about 0.005 wt. % to about 0.5 wt. % based on the total weight of the composition, and further optionally, from about 0.01 wt. % to about 0.1 wt. % based on the total weight of the composition.

Optionally, the oral care composition further comprises one or more agents selected from an anti-plaque agent, a whitening agent, a sweetening agent, a cleaning agent and a flavouring agent.

Typically, the oral care composition comprises an orally acceptable carrier for a toothpaste, a dental cream, a mouthwash, a chewing gum or a denture adhesive.

Typically, the oral care composition is suitable for preventing or treating a disease condition of the oral cavity.

Optionally, the disease condition is selected from dental plaque, tooth decay, periodontal disease or gingivitis.

In a second aspect, the present invention provides an oral care composition comprising a glucose antimetabolite in an amount of less than about 0.7 wt. % based on the total weight of the composition for inhibiting microbial biofilm formation and/or degrading microbial biofilm.

In a third aspect, the present invention provides a method of inhibiting microbial biofilm formation and/or degrading a microbial biofilm in the oral cavity of a subject comprising administering to the subject a composition comprising a glucose antimetabolite.

Typically, in the method of the present invention, the glucose antimetabolite is present in the composition at a concentration of less than about 1 wt. % based on the total weight of the composition.

Optionally, in the method of the present invention, the glucose antimetabolite is present in the composition at a concentration of less than about 0.7 wt. % based on the total weight of the composition.

Further optionally, in the method of the present invention, the glucose antimetabolite is present in the composition at a concentration of from about 0.005 wt. % to about 0.5 wt. % based on the total weight of the composition, and still further optionally, from about 0.01 wt. % to about 0.1 wt % based on the total weight of the composition.

In the method of the present invention, the composition further optionally comprises one or more agents selected from an anti-plaque agent, a whitening agent, a sweetening agent, a cleaning agent and a flavouring agent. Further optionally, the composition comprises an orally acceptable carrier for a toothpaste, a dental cream, a mouthwash, a chewing gum or a denture adhesive.

Typically, the method of the present invention comprises preventing or treating a disease condition of the oral cavity. Optionally, the disease condition is selected from dental plaque, tooth decay, periodontal disease or gingivitis.

Optionally, in the method of the present invention, the biofilm comprises one or more species of bacteria selected from *Actinomyces viscosus, Lactobacillus casei, Streptococcus oralis, Fusobacterium nucleatum* and *Veillonella parvula*, and *Porphiromonas gingivalis*. The biofilm can comprise other bacterial species which include, but are not limited to the species described in Paster et al., "Bacterial diversity in human subgingival plaque", *J. Bacteriology*, 183(12): 3770-3783 (June 2001) and Dewhirst et al., "The human oral microbiome", *J. Bacteriology*, 192(19): 5002-5017 (October 2010), which are incorporated herein by reference.

In a fourth aspect, the present invention provides the use of a glucose antimetabolite, in an oral care composition, for inhibiting microbial biofilm formation and/or degrading microbial biofilm in the oral cavity of a subject.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range.

In addition, all references cited herein are hereby incorporated by referenced in their entireties. In the event of a conflict in a definition in the present disclosure and that of a cited reference, the present disclosure controls.

As used herein, "antimetabolite" refers to any substance that replaces or inhibits an organism's utilization of a metabolite.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

In some embodiments, the present invention provides an oral care composition comprising a deoxy sugar antimetabolite in an amount of less than about 0.7 wt. % based on the total weight of the composition. In other embodiments, the present invention provides a method of inhibiting microbial biofilm formation and/or degrading a microbial biofilm in the oral cavity of the subject comprising administering to the subject a composition comprising a deoxy sugar antimetabolite.

Biofilm

The term "biofilm" used in the context of the present invention means any group of microorganisms encapsulated within a self-developed polymeric extracellular matrix. The biofilm may be adhered to a living or inert surface. For example, in the oral cavity, the biofilm may be adhered to teeth in the form of plaque.

The biofilm may be formed from one or more different types of microorganisms including for example bacteria, archaea, protozoa, fungi and algae. The biofilm is preferably formed from bacteria. In one embodiment the biofilm is formed from a single species of bacteria. In another embodiment, the biofilm is formed from a plurality of species of bacteria.

In another embodiment, the biofilm may be formed from one or more bacteria selected from The biofilm may be formed from one or more bacteria selected from *Actinomyces viscosus, Lactobacillus casei, Streptococcus oralis, Fusobacterium nucleatum, Veillonella parvula* and *Porphyromonas gingivalis.*

Deoxy Sugar Antimetabolite

The deoxy sugar antimetabolite of the present invention may be any substance that replaces or inhibits an organism's utilization of glucose or carbohydrates containing glucose (e.g. starch, sucrose (table sugar), amylose, amylopectin, pullulan, etc.). Typically, the deoxy sugar antimetabolite bears close structural resemblance to the corresponding metabolite and is utilized in place of the metabolite in physiological reactions, thereby preventing normal physiological reactions.

In one embodiment of the invention, the deoxy sugar antimetabolite comprises the compound of formula (I).

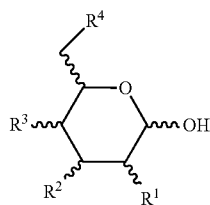
(I)

wherein:
$R_1$ is H, OH, $CH_3$, $NH_2$ or halogen;
$R_2$ is H. OH, $CH_3$, $NH_2$ or halogen;
$R_3$ is H, OH, $CH_3$, $NH_2$ or halogen;
$R_4$ is H, OH, $NH_2$ or halogen; and
at least three of $R_1$, $R_2$, $R_3$ and $R_4$ is OH.

In another embodiment of the invention, the deoxy sugar antimetabolite is the compound of formula (I) wherein:
$R_1$ is H, OH, $CH_3$, $NH_2$. F or Cl;
$R_2$ is H, OH, $CH_3$, $NH_2$, F or Cl;
$R_3$ is H, OH, $CH_3$, $NH_2$, F or Cl:
$R_4$ is H, OH, $NH_2$, F or Cl; and
at least three of $R_1$, $R_2$, $R_3$ and $R_4$ is OH.

In another embodiment of the invention, the deoxy sugar antimetabolite is the compound of formula (I) wherein:
$R_1$ is H, OH, $CH_3$, $NH_2$, F or Cl;
$R_2$ is H, OH, $CH_3$, $NH_2$, F or Cl;
$R_3$ is H, OH, $CH_3$, $NH_2$, F or Cl;
$R_4$ is H, OH, $NH_2$, F or Cl; and
at least three of $R_1$, $R_2$, $R_3$ and $R_4$ is OH.

In another embodiment of the invention, the deoxy sugar antimetabolite is the compound of formula (I) wherein:
$R_1$ is H, OH, or F;
$R_2$ is H, OH, or F;
$R_3$ is H, OH, or F;
$R_4$ is H, OH, or F; and
at least three of $R_1$, $R_2$, $R_3$ and $R_4$ is OH.

In one embodiment of the invention, the deoxy sugar antimetabolite comprises a compound of formula (II)-(V).

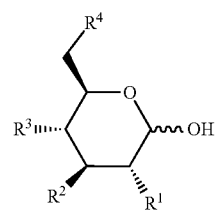
(II)

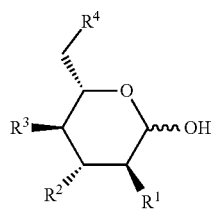
(III)

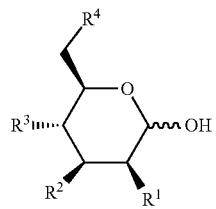
(IV)

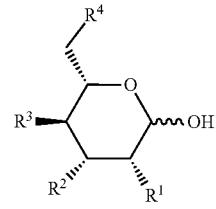
(V)

wherein:
$R_1$ is H, OH, $CH_3$, $NH_2$ or halogen;
$R_2$ is H, OH, $CH_3$, $NH_2$ or halogen;
$R_3$ is H, OH, $CH_3$, $NH_2$ or halogen;
$R_4$ is H, OH, $NH_2$ or halogen; and
at least three of $R_1$, $R_2$, $R_3$ and $R_4$ is OH.

In another embodiment of the invention, the deoxy sugar antimetabolite is the compound of formula (II)-(V) wherein:
$R_1$ is H, OH, $CH_3$, $NH_2$, F or Cl;
$R_2$ is H, OH, $CH_3$, $NH_2$, F or Cl;
$R_3$ is H, OH, $CH_3$, $NH_2$, F or Cl;
$R_4$ is H, OH, $NH_2$, F or Cl; and
at least three of $R_1$, $R_2$, $R_3$ and $R_4$ is OH.

In another embodiment of the invention, the deoxy sugar antimetabolite is the compound of formula (II)-(V) wherein:
$R_1$ is H, OH, $CH_3$, $NH_2$, F or Cl;
$R_2$ is H, OH, $CH_3$, $NH_2$, F or Cl;
$R_3$ is H, OH, $CH_3$, $NH_2$, F or Cl;
$R_4$ is H, OH, $NH_2$, F or Cl; and
at least three of $R_1$, $R_2$. $R_3$ and $R_4$ is OH.

In another embodiment of the invention, the deoxy sugar antimetabolite is the compound of formula (II)-(V) wherein:
$R_1$ is H, OH, or F;
$R_2$ is H, OH, or F;
$R_3$ is H, OH, or F;
$R_4$ is H, OH, or F; and
at least three of $R_1$, $R_2$, $R_3$ and $R_4$ is OH.

In one embodiment of the invention, the deoxy sugar antimetabolite comprises a compound of formula (II)

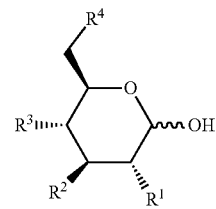
(II)

wherein:
$R_1$ is H, OH, $CH_3$, $NH_2$ or halogen;
$R_2$ is H, OH, $CH_3$, $NH_2$ or halogen;
$R_3$ is H, OH, $CH_1$, $NH_2$ or halogen;
$R_4$ is H, OH, $NH_2$ or halogen; and
at least three of $R_1$, $R_2$, $R_3$ and $R_4$ is OH.

In another embodiment of the invention, the deoxy sugar antimetabolite is the compound of formula (II) wherein:
$R_1$ is H, OH, $Cl_3$, $NH_2$, F or Cl;
$R_2$ is H, OH, $CH_3$, $NH_2$, F or Cl;
$R_3$ is H, OH, $CH_3$, $NH_2$, F or Cl;
$R_4$ is H, OH, $NH_2$, F or Cl; and
at least three of $R_1$, $R_2$, $R_3$ and $R_4$ is OH.

In another embodiment of the invention, the deoxy sugar antimetabolite is the compound of formula (II) wherein:
$R_1$ is H, OH, $CH_3$, $NH_2$. F or Cl;
$R_2$ is H, OH, $CH_3$, $NH_2$, F or Cl;
$R_3$ is H, OH, $CH_3$, $NH_2$, F or Cl;
$R_4$ is H, OH, $NH_2$, F or Cl; and
at least three of $R_1$, $R_2$, $R_3$ and $R_4$ is OH.

In another embodiment of the invention, the deoxy sugar antimetabolite is the compound of formula (II) wherein:
$R_1$ is H, OH, or F;
$R_2$ is H, OH, or F;
$R_3$ is H, OH, or F;
$R_4$ is H, OH, or F; and
at least three of $R_1$, $R_2$, $R_3$ and $R_4$ is OH.

In another embodiment of the invention, the deoxy sugar antimetabolite is an antimetabolite selected from the group consisting of 6-deoxy-D-glucose, 2-fluoro-2-deoxy-D-glucose or mannosamine (2-amino-2-deoxy-D-mannose). In another embodiment of the invention, the glucose antimetabolite comprises 6-deoxy-D-glucose, 2-fluoro-2-deoxy-D-glucose.

In another embodiment of the invention, the above described deoxy sugars includes a proviso excluding 2-deoxy-D-glucose (formula (II), wherein $R_1$ is H and $R_2$, $R_3$ and $R_4$ are OH) and 2-amino-2-deoxy-D-glucose (glucosamine—formula (II), wherein $R_1$ is $NH_2$ and $R_2$, $R_3$, and $R_4$ are OH)

Salt forms for the various embodiments of the deoxy sugar antimetabolites described above are also intended to be encompassed. Also intended to be encompassed are the D- and L-forms, open chain and ring forms, and the alpha- and beta-anomers of the deoxy sugar antimetabolites.

Typically, the deoxy sugar antimetabolite is present in the composition in an amount of less than 0.7 wt. %, based on the total weight of the composition. In some embodiments, the deoxy sugar antimetabolite is present in the composition at a concentration of from about 0.005 wt. % to about 0.5 wt. % based on the total weight of the composition, or from about 0.008 wt. % to about 0.3 wt. % based on the total weight of the composition.

Optionally, the deoxy sugar antimetabolite is present in the composition at a concentration of from about 0.005 wt. % to about 0.05 wt. % based on the total weight of the composition, or from about 0.008 wt. % to about 0.03 wt. % based on the total weight of the composition. In some embodiments, the deoxy sugar antimetabolite is present in the composition in an amount of from about 0.009 wt. % to about 0.0125 wt. %.

Oral Care Compositions

An embodiment of the oral care composition of the invention comprises an orally acceptable carrier in a product such as dentifrice, mouthwash, mouthrinse, toothpaste, gel, dental cream, chewing gum, or portable dosage article such as, without limitation, a lozenge, a mint, bead, wafer, liquid formulated for oral application in a small portable nebulizer (spray bottle), liquid formulated for oral application in a small portable drop-generating bottle, or a soft pliable tablet ("chewie"). As used herein, an "orally acceptable carrier" refers to a material or combination of materials that are safe for use in the compositions of the invention, commensurate with a reasonable benefit/risk ratio.

In one embodiment of the invention, the oral care composition does not contain any additional antibacterial or antimicrobial compound except for the deoxy sugars described above.

The composition according to the present invention may also comprise one or more further agent(s) which is or are operably for the prevention or treatment of a condition or a disorder of hard or soft tissue of the oral cavity, the prevention or treatment of a physiological disorder or condition, or which provide(s) a cosmetic benefit.

The further agents are typically selected from an antiplaque agent, a whitening agent, cleaning agent, a flavoring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agents, an antisensitivity agent, an antioxidant agent, nutrients, viscosity modifiers, diluents, opacifiers, breath freshening agents and zinc salts and combinations thereof. It is understood that while general attributes of each of the above categories of materials may differ, there may be some common attributes, and any given material may serve multiple purposes within two or more of such categories of materials. Preferably, the carrier is selected for compatibility with other ingredients of the composition.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone. [alpha]-irisone, propenyl guaiethol, thymol, linalool, benzaldehyde, cinnamaldehyde. N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01 wt. % to about 5 wt. %, optionally in various embodiments from about 0.05 to about 2 wt. %, from about 0.1 wt. % to about 2.5 wt. %, and from about 0.1 to about 0.5 wt. %.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition.

Colorants among those useful herein include pigments, dyes, flakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001 wt. % to about 20 wt. %, for example about 0.01 wt. % to about 10 wt. % or about 0.1 wt. % to about 5 wt. %.

The compositions of the present invention further comprise an optional abrasive useful for example as a polishing agent. In one embodiment of the invention, the abrasive include, but are not limited to silica, calcined alumina, sodium bicarbonate, calcium carbonate, dicalcium phosphate and calcium pyrophosphate may be included in the base dentifrice compositions used in the practice of the present invention. Other abrasives may also be suitable for use in the compositions described herein. Visually clear dentifrice compositions may be obtained by using an abrasive such as collodial silica, e.g., those sold under the trade designation Zeodent 115 available from the Huber Corporation or alkali metal aluminosilicate complexes (that is, silica containing alumina combined in its matrix) which have refractive indices close to the refractive indices of gelling agent-liquid (including water and/or humectant) systems used in dentifrice compositions. The abrasive is generally present in the base dentifrice composition in weight concentrations of about 3% to about 50% by weight.

Some embodiments provide oral care compositions comprising from about 5 to about 15 wt. % abrasive based on the total weight of the composition.

When abrasives are present, the average particle size is generally about 0.1 to about 30 microns, for example about 1 to about 20 or about 5 to 15 microns.

Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In one embodiment of the invention, the viscosity modifier (thickener) include, but are not limited to amorphous silicas available from Huber Corporation under the trade designation Zeodent 165, Irish moss, iota-carrageenan, polyvinylpyrrolidone, carboxyvinyl polymers, cellulosic polymers such as hydroxyethyl cellulose, carboxymethyl cellulose (carmellose) and salts thereof (e.g., carmellose sodium), natural gums such as karaya, gum arabic and tragacanth, colloidal magnesium aluminum silicate, colloidal silica and mixtures thereof. Optionally, one or more thickening agents are optionally present in a total amount of about 0.01% to about 15%, in some embodiments about 0.1% to about 10%, in some embodiments about 0.10 to about 5% by weight, in some embodiments about 0.2% to about 5% by weight and in some embodiments about 0.2 to about 1% by weight.

In one embodiment of the invention the composition comprise a tartar control (anticalculus) agent which include, but are not limited to salts of any of these agents, for example their alkali metal and ammonium salts:phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

Fluoride salts and fluoride ion sources, e.g., fluoride salts which may be soluble, are known in the art and may be incorporated into the compositions of the present invention. Representative fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention optionally incorporate one or more antisensitivity agents, e.g., potassium salts such as potassium nitrate, potassium bicarbonate, potassium chloride, potassium citrate, and potassium oxalate; capsaicin; eugenol; strontium salts; zinc salts, chloride salts and combinations thereof. Such agents may be added in effective amounts, e.g., from about 1 wt. % to about 20 wt. % by weight based on the total weight of the composition, depending on the agent chosen. The compositions of the present invention may also be used to treat hypersensitivity by blocking dentin tubules when applied to a tooth.

The compositions of the present invention may also include a tooth whitening or tooth bleaching composition, which are known in the art. Suitable whitening and bleaching composition include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., from about 1 wt. % to about 20 wt. % by weight based on the total weight of the composition, depending on the agent chosen.

In some embodiments, the compositions of the invention further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In some embodiments, the compositions of the present invention further comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

The compositions of the present invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

In one embodiment of the invention, the saliva stimulating agent include, but are not limited to a saliva stimulating agent, useful for example in amelioration of dry mouth, may be included. Any orally acceptable saliva stimulating agent can be used, including without limitation food acids such as citric, lactic, malic, succinic, ascorbic, adipic, fumaric, and tartaric acids, and mixtures thereof.

In one embodiment of the invention, the pH modifying agent includes, but is not limited to, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range.

In one embodiment of the invention, the antiplaque (e.g., plaque disrupting) agent includes, but is not limited to stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof In one embodiment of the invention, breath freshening agents include, but are not limited to zinc salts (which in turn include, but are not limited to zinc acetate, zinc borate, zinc butyrate, zinc carbonate, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof), alpha-ionone and mixtures thereof. One or more breath freshening agents are optionally present in a breath freshening effective total amount.

In various embodiments, the oral composition according to the present invention is not intentionally swallowed, but is rather retained in the oral cavity for a time sufficient to effect the intended utility. In other portable embodiments (such as a lozenge, mint, bead, wafer, liquid formulated for oral application from a small portable nebulizer, liquid formulated for oral application from a small portable drop-generating bottle, or a soft pliable tablet), the oral composition is intentionally swallowed, optionally after retention in the oral cavity for a time sufficient to effect intended utility.

The composition according to the present invention preferably comprises an orally acceptable carrier in a product such as mouthwash, toothpaste, dental cream, chewing gum, denture adhesive or portable dosage article such as, without limitation, a lozenge, a mint, bead, wafer, liquid formulated for oral application in a small portable nebulizer (spray bottle), liquid formulated for oral application in a small portable drop-generating bottle, or a soft pliable tablet ("chewie"). As used herein, an "orally acceptable carrier" refers to a material or combination of materials that are safe for use in the compositions of the present invention, commensurate with a reasonable benefit/risk ratio.

The present invention also provides portable dose article comprising an oral care composition as defined above, wherein the portable dose article is selected from a lozenge, a mint, a bead, a wafer, a small portable nebulizer containing said admixture in liquid formulated for oral application as a spray, a small portable bottle containing said admixture in liquid formulated for oral application as a drop, and a soft pliable tablet.

Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable". "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

All of the ingredients in the compositions may have functions in addition to their primary function, and may contribute to the overall properties of the composition, including stability, efficacy, consistency, mouthfeel, taste, odor and so forth.

Methods of Use

The composition according to the present invention may be administered to or applied to a human or other animal subject. The composition may be suitable for administration or application to the oral cavity of a human or animal subject. Typically, the composition is for inhibiting microbial biofilm formation and/or degrading microbial biofilm.

The present invention further provides a composition as defined above for preventing or treating a disease condition of the oral cavity. Typically, the disease condition is caused by biofilm formation. The disease condition may be selected from dental plaque, tooth decay, periodontal disease and gingivitis.

Accordingly, the present invention provides a composition as defined above for use as a medicament, and in particular, for use in inhibiting microbial biofilm formation and/or degrading microbial biofilm.

The present invention also provides a method of inhibiting microbial biofilm formation and/or degrading a microbial biofilm in a subject comprising administering to the subject a composition comprising a deoxy sugar antimetabolite. Preferably, the composition is an oral care composition as defined herein, and the composition is applied to an oral cavity. In a preferred embodiment, the method is for treating or preventing a condition caused by biofilm formation. Preferably, the condition caused by biofilm formation is a condition of the oral cavity and may be selected from dental plaque, tooth decay, periodontal disease and gingivitis.

The present invention further provides a use of a deoxy sugar antimetabolite, in an oral care composition, for inhibiting microbial biofilm formation and/or degrading a microbial biofilm in the subject. Preferably, the use comprises inhibiting microbial biofilm formation and/or degrading a microbial biofilm in the oral cavity of a subject.

In one embodiment of the invention, use of a deoxy sugar metabolite decreases bacteria by less than 5% or less than 2% or less than 1%.

In another embodiment of the invention, use of a deoxy sugar metabolite reduces or inhibits biofilm formation by at least 25% or at least 40% or at least 60%.

In another embodiment use of a deoxy sugar metabolite has a biofilm efficiency of at least 1000% (biofilm efficiency defined as (% biofilm inhibition/% bacteria reduction)×100%)).

A composition comprising a deoxy sugar antimetabolite is capable of significantly inhibiting biofilm formation and/or degrading an existing biofilm in a subject. The composition is particularly useful for inhibiting biofilm formation and/or degrading a biofilm in the oral cavity. Additionally, the deoxy sugar antimetabolites do not kill the bacteria and therefore do not have the disadvantages of traditional antimicrobial agents, like developing resistance while maintaining healthy microflora in the oral cavity. The ability to inhibit biofilm formation means that bacteria in the mouth will be less protected and therefore more susceptible to traditional removal/killing.

A medicament comprising the composition according to the present invention may be administered to a patient. The deoxy sugar antimetabolite may effectively inhibit biofilm formation and/or degrade a biofilm without being incompatible or unstable with other oral care active ingredients and without inactivating other desirable additional oral care ingredients, whilst easily delivered in vivo.

In one embodiment of the invention, the patient in need of reduction or inhibition of biofilm formation suffers from gingivitis or periodontitis. In turn, the method of treatment can also be directed toward the treatment of gingivitis or periodontitis.

EXAMPLES

Example 1—Healthy Biofilms 0.5" $Ca^{2+}$-deficient hydroxyapatite (HAP) disks were coated with UV-sterilized human saliva overnight. The saliva-coated HAP (scHAP) disks were treated for 1 hour with solutions of a test compound (0.01% 2-deoxy-D-glucose) or a control compound ((0.01%) of cetylpyridinium chloride (CPC)) to allow for uptake and coating of the disks with the potential active ingredient.

After 1 hour, excess treatment was removed by aspiration and disks were inoculated with 1 ml of bacteria from a continuous culture system at an OD(600) of about 0.2. The continuous culture system was maintained for approximately three months at 37° C. and contained five representative oral bacterial species: *A. viscosus, L. casei, S. oralis, V. parvula* and *F. nucleatum*. Previous work has shown this mix to form repeatable biofilms that can serve as a representation of the more complex mix of 500-700 bacterial species found in dental plaque.

The inoculated scHAP disks were incubated for 48 hours at 37° C. to allow a biofilm to form on them. After 48 hours of biofilm formation, disks were transferred to test tubes containing 1 ml of 0.25% trypsin solution. Disks were incubated at 37° C. with shaking for 45 minutes. The tubes were briefly vortexed to resuspend the bacteria, and the supernatants were then transferred to a fresh 24 well plate. Plates were sonicated for 2 minutes to pellet any residual HAP flakes and the supernatants were removed to fresh plates so that their absorbance could be measured at 610 nm. All samples were tested in triplicate and the average of the three wells was determined.

In addition to the absorbance of the trypsin-digested resuspended bacterial solution, similar absorbance measurements were also taken of the final supernatant media after the biofilms were allowed to grow for 48 hours. This gave an indication of whether or not the active ingredient had an antibacterial effect and prevented growth of the bacterial population.

The effect of 2-deoxy-D-glucose on bacterial growth in the supernatant media in which the biofilms were grown is shown in the table below. CPC (cetylpyridinium chloride), which is a potent antibacterial agent commonly found in a variety of oral care products, especially mouthwashes, acted as a positive control for the experiment. CPC is typically used at levels around 0.075% in mouthwashes but previous studies have shown that 0.01% CPC in solution is a very effective antibacterial agent.

TABLE 1

| Compound (0.01 wt. %) | % bacterial reduction (A) | % biofilm inhibition (B) | % biofilm inhibition efficiency (C) |
|---|---|---|---|
| CPC | 65.44 | 32.69 | 50.00 |
| Triclosan | 85.63 | 52.23 | 60.99 |
| Benzalkonium chloride | 88.21 | 52.58 | 59.61 |
| DL-5-hydroxylysine HCl | 21.45 | 5.85 | 27.27 |
| 2-deoxy-D-glucose | 9.81 | 30.54 | 311.31 |
| 6-deoxy-D-glucose | 1.54 | 25.33 | 1644.81 |
| 2-fluoro-2-deoxy-D-glucose | 0.00 | 46.50 | >>>1000 |

% bacterial reduction and % biofilm inhibition reflect percentage reduction in absorbance relative to disks treated with media alone.

Despite the high degree of inhibition of bacterial growth demonstrated with 0.01% CPC, triclosan, and benzalkonium chloride in the table above, these compounds had relatively mediocre biofilm inhibition efficiency (C), where C=B/A× 100%. DL-5-hydroxyllysine HCL had significant bacterial reduction, but also had negligible biofilm inhibition. 2-deoxy-D-glucose was more effective as an inhibitor of biofilm formation, but still displayed nearly 10% bacterial reduction.

In contrast, 6-deoxy-D-glucose and 2-fluoro-2-deoxy-D-glucose, both displayed biofilm inhibition far greater than what would have been predicted from their bacterial reduction. Thus, it may be concluded that 6-deoxy-D-glucose and 2-fluoro-2-deoxy-D-glucose is an effective and efficient inhibitor of biofilm formation which can also maintain healthy microflora.

Example 2—Healthy Biofilms

A similar test protocol to Example 1 was performed and tested for its effect in the inhibition of planktonic growth and inhibition of biofilm formation The species used for biofilm formation were: *Actinomyces naeslundii* (ATCC 43146). *Lactobacillus casei* (ATCC 334), *Streptococcus oralis* (ATCC 35037), *Veillonella parvula* (ATCC 17745) and *Fusobacterium nucleatum* (ATCC 10953). Strains were grown under anaerobic conditions at 37° C. for 72 hours. All the bacteria were grown on an anaerobic blood agar.

The formula for the anaerobic blood agar was as follows: 52 g/l Brain Heart Infusion Agar (DIFCO), and after autoclaving the following products are added: 1 ml/l baemin from a solution 5 mg/ml, 1 ml/l of vitamin K1 from a solution 100 µg/ml and 50 ml of horse blood. A 24 well microtiter for cell culture (Nalgene Nunc International, Denmark) was used to generate in vitro dental biofilms.

Wells were filled with 800 µl of the mucin growth medium (MGM), a modification of the medium used by Kinniment et al. (Kinniment, S. L., Wimpenny. J. W., Adams, D., and Marsh, P. D. (1996) Development of a steady-state oral microbial biofilm community using the constant-depth film fermenter. Microbiology 142 (Pt 3): 631-638) which presents a high concentration of proteins: 2.5 g/l mucin, 5 g/l Heart Infusion Broth (DIFCO), 2.0 g/l sodium bicarbonate, 1.0 g/l yeast extract and 0.1 g/l cysteine and 4 ml resazurin from a solution 25 mg/100 ml.

The pH is adjusted to 7.4 prior to autoclaving. After autoclaving the following products was added: 1 ml/l haemin from a solution 5 mg/ml and 1 mL/l of vitamin K1 from a solution 100 µg/ml. Sterile hydroxyapatite discs of 7 mm×1.8 mm (Clarkson Inc., USA) was later placed into the wells. In order to form the acquired pellicle the discs were allowed to stay at least 60 hours in contact with the medium under anaerobic conditions prior inoculation. This period of pre-incubation allows checking for possible contaminations and adjusts the final pH to 7.5.

Each of the strains grown on agar was resuspended in MGM medium until reach a turbidity of a McFarlan 3 (approximately $10^8$ CFU/ml). Finally, 1 ml of each suspension from the different strains was mixed and 50 µl of this suspension was added into each of the wells in the microtiter plate. Microtiter plates were incubated under anaerobic conditions at 37° C. in an anaerobic chamber. A control of growth was performed in parallel. 25 µl of each suspension used for preparing the inoculum was dropped onto a plate of anaerobic blood agar and was incubated under anaerobic conditions at 37° C. in an anaerobic chamber to check for viability.

After 24 hours planktonic phase was saved to measure growth at OD600 and hydroxyapatite disks were washed with sterile PBS and stained with safranine 0.1% for 15 minutes. After that period of time disks were washed twice in distilled water and safranine from the stained biofilm was released with 95% ethanol/1 % SDS solution. Absorbance at 492 nm measures the amount of safranine retained by the biofilm.

TABLE 2

| Compound (0.01 wt. %) | % planktonic growth inhibition | % biofilm inhibition |
|---|---|---|
| DL-5-hydroxylysine HCl | 0.00 | 5.91 |
| D-mannosamine (2-amino-2-deoxy-D-mannose) | 0.00 | 34.01 |

Similar to the bacterial reduction/biofilm inhibition of Example 1, DL-5-hydroxylysine HCl showed no planktonic growth inhibition, but also showed minimal biofilm inhibition. In contrast, D-mannosamine showed an effective inhibition of biofilm formation and would be expected to maintain healthy microflora.

Example 3—Pathogenic Biofilms

A similar experiment was conducted using a pathogenic biofilm model. Biofilms were inoculated as above for the healthy biofilms. Initial bacterial attachment and biofilm formation was allowed to proceed for 4 hours. After the initial 4 hours, each biofilm was spiked with 100 µL of an overnight culture of *P. gingivalis*. Biofilms were then allowed to grow for another 48 hours prior to trypsin treatment, and absorbance measurements were taken as described above.

Overall, these results indicate that deoxy sugar antimetabolite antimicrobial agents, e.g. 6-deoxy-D-glucose and 2-fluoro-2-deoxy-D-glucose, are very good inhibitors of oral biofilm formation and shows that this approach has an enhanced effect on the integration of disease-causing organisms into the biofilm, i.e. having the potential to prevent the progression of the disease beyond simply killing the bacteria.

Example 4—Oral Care Composition

A representative oral care composition of the invention is depicted as toothpaste composition in the table below:

| Ingredient | % wt/wt. |
|---|---|
| Sorbitol | 66-71 |
| Water | 7-13 |
| Polyethylene glycol | 0.5-1.5 |
| Silica | 12-20 |
| Sodium lauryl sulfate (SLS) | 0.5-2.5 |
| Sodium fluoride | 0.1-0.3 |
| Flavor | 0.5-2.5 |
| Carboxymethyl cellulose (CMC) | 0.3-0.9 |
| Sodium saccharin | 0.3-0.9 |
| Deoxy sugar antimetabolite | 0.3-0.9 |
| CAP-betaine | 0.1-0.6 |
| Total | 100.00 |

As those skilled in the art will appreciate, numerous changes and modifications may be made to the embodiments described herein without departing from the spirit of the invention. It is intended that all such variations fall within the scope of the appended claims.

The invention claimed is:

1. A method of inhibiting microbial biofilm formation and/or degrading a microbial biofilm in the oral cavity of a subject comprising administering to the subject an oral care composition comprising a deoxy sugar antimetabolite with no additional antibacterial agent and an orally acceptable carrier, wherein the deoxy sugar antimetabolite is present in the composition at a concentration of from 0.005% to 0.7% based on the total weight of the composition, wherein bacteria is decreased by less than 5% and biofilm is inhibited by at least 25%, and wherein the deoxy sugar antimetabolite is selected from the group consisting of 6-deoxy-D-glucose, 2-fluoro-2-deoxy-D-glucose, 2-amino-2-deoxy-D-mannosamine, and mixtures thereof.

2. The method of claim 1, wherein the deoxy sugar antimetabolite is selected from the group consisting of 6-deoxy-D-glucose, 2-fluoro-2-deoxy-D-glucose, and mixtures thereof.

3. The method of claim 1, wherein the deoxy sugar antimetabolite is 2-amino-2-deoxy-D-mannosamine.

4. The method of claim 1, wherein the biofilm efficiency is at least 1000%.

5. The method according to claim 1, wherein the method comprises treats a disease condition of the oral cavity by inhibiting microbial biofilm formation and/or degrading a microbial biofilm in the oral cavity which is selected from the group consisting of dental plaque, tooth decay, periodontal disease and gingivitis.

6. The method according to claim 1, wherein the biofilm is formed from one or more species of bacteria selected from *Actinomyces viscosus, Actinomyces naeslundii, Lactobacillus casei, Streptococcus oralis, Fusobacterium nucleatum* and *Veillonella parvula*, and *Porphyromonas gingivalis*.

7. The method of claim 1, wherein the deoxy sugar antimetabolite is 6-deoxy-D-glucose.

8. The method of claim 1, wherein the deoxy sugar antimetabolite is 2-fluoro-2-deoxy-D-glucose.

9. The method of claim 1, wherein the deoxy sugar antimetabolite is present in the composition at a concentration of from 0.005% to 0.5% based on the total weight of the composition.

10. The method of claim 1, wherein the deoxy sugar antimetabolite is present in the composition at a concentration of from 0.008% to 0.3% based on the total weight of the composition.

* * * * *